US005618315A

United States Patent [19]

Elliott

[11] Patent Number: 5,618,315

[45] Date of Patent: Apr. 8, 1997

[54] SPINAL AND OTHER OSSEOUS JOINT ADJUSTING INSTRUMENT

[75] Inventor: Thomas Elliott, Tulsa, Okla.

[73] Assignee: Elliott Family Trust, Tulsa, Okla.

[21] Appl. No.: 371,130

[22] Filed: Jan. 11, 1995

[51] Int. Cl.[6] .......... A61F 5/00

[52] U.S. Cl. .......... 606/237; 606/238; 601/108

[58] Field of Search .......... 601/48, 84, 107, 601/108, 109, 110, 111; 606/237, 238

[56] References Cited

U.S. PATENT DOCUMENTS

| | | |
|---|---|---|
| D. 223,419 | 4/1972 | Pettibon . |
| 2,048,220 | 7/1936 | Redding . |
| 4,116,235 | 9/1978 | Fuhr et al. . |
| 4,338,723 | 7/1982 | Benjamin . |
| 4,461,286 | 7/1984 | Sweat . |
| 4,549,535 | 10/1985 | Wing . |
| 4,841,955 | 6/1989 | Evans et al. . |
| 5,224,469 | 7/1993 | Mocny . |

FOREIGN PATENT DOCUMENTS

| | | |
|---|---|---|
| 557680 | 8/1932 | Germany . |

*Primary Examiner*—Michael Powell Buiz
*Assistant Examiner*—Mark S. Leonardo
*Attorney, Agent, or Firm*—Head, Johnson & Kachigian

[57] ABSTRACT

An instrument for adjusting vertebrae and other osseous joint subluxation and luxations comprising a device for generating a complex energy waveform, of varying frequency and amplitude, to be applied to the patient in the proximity of the vertebrae or other joints to be adjusted comprising a hand held portion with a moveable stylus at one end, which imparts lateral and torque components of energy, a stylus driving apparatus, a display array to indicate proper alignment of the hand held portion and a pistol grip for ease of handling of the hand held portion; and a fixed controller portion which is used to program the proper alignment of and energy to be applied via the stylus in the hand held portion, and the method for adjusting vertebrae and other osseous joint subluxation and luxations using the said complex energy waveform.

8 Claims, 2 Drawing Sheets

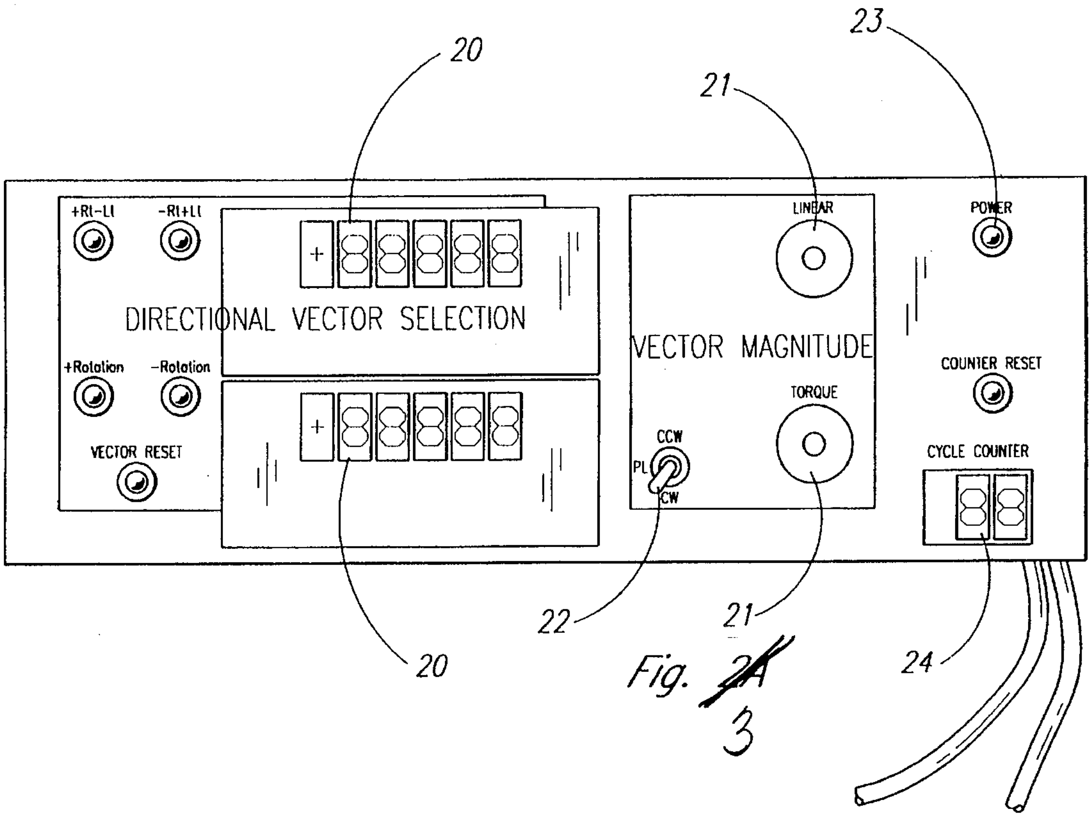
Fig. ~~2A~~ 3
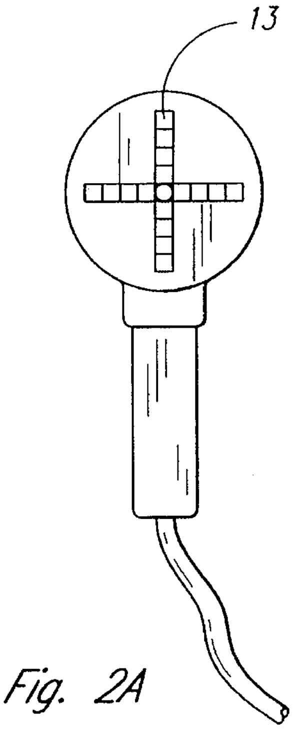
Fig. 2A
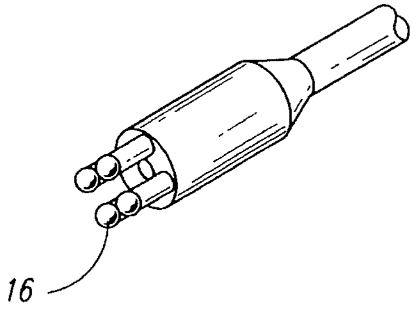
Fig. 4

SPINAL AND OTHER OSSEOUS JOINT ADJUSTING INSTRUMENT

BACKGROUND OF THE INVENTION

1. Field of the Invention

The present invention describes a spinal and other osseous joint adjusting instrument and more particularly to a device that may be programmed to apply a plurality of controlled force impulses in a precise manner and at a predetermined location according to the unique needs of a particular patient.

Various adjusting instruments have heretofore been developed for chiropractic practice. Those heretofore have been limited in that they were primarily intended as a substitute for manual force thrust application. Redding U.S. Pat. No. 2,048,220, Fuhr et al. U.S. Pat. No. 4,116,235, and Sweat U.S. Pat. No. 4,461,286 describe a spring mounted means for moving a plunger to apply a linear or sometimes a linear and radial force. Evans et al. U.S. Pat. Nos. 4,841,955 and 4,984,127, use a solenoid means to achieve similar motion. Each of the previous inventions attempt to replace the human method of treating vertebrae subluxation. Each of these devices are fixed frequency single impact devices, and therefore limited in their efficacy. Furthermore they lack alignment features thus making it difficult to ascertain proper positioning of the instrument.

SUMMARY OF THE INVENTION

The present invention describes an instrument for the adjustment or manipulation of the osseous members of human patients and vertebrate animals. The instrument can deliver a force consisting of both linear and torque components and is intended to be of particular assistance in the practice of chiropractic. By linear force we mean force in the direction of the axis of the instrument. By torque we mean force in a radial or twisting motion about the axis of the instrument which may be in either a clockwise or counterclockwise direction. In this invention the force applied is not a single impact, to be repeated according to the judgement of the practitioner, but rather a complex energy wave designed to include the natural harmonic frequencies of the patient. Thus one application consists of a series of pressure waves at a frequency from about 10 to 80 hertz. The present invention further allows for precise positioning of the direction fox the delivery of the complex wave energy in accordance with previously measured subluxation on the particular patient being treated, as well as the adjustment of the amplitude of the force, the relative amplitudes of the linear and torque components and the direction of the torque component.

It is well known in the chiropractic art that misalignments of the spine, particularly the cervical spine and the first vertebra thereof, may cause the patient to have symptoms of various infirmities. The seduction of such subluxation has been demonstrated to relieve such symptoms and reduce the discomfort suffered by the patient. Many other adverse symptoms are due to the dislocation of other osseous joints, which are amenable to relief by the adjustment or repositioning of such joints to avoid dislocation.

Chiropractic practice calls for treatment of subluxation by typically manual adjustments. Practitioners must develop extreme manual dexterity and muscular development in their hands, arms and shoulders in order to be effective in administering such treatment manually. The use of instruments and particularly this invention reduces the stress and training required of the practitioner, and enables the chiropractor to achieve quantifyable, measurable, repetitive results with minimum discomfort to the patient.

The usual method of treatment, is to first establish the nature and amount of subluxation which is typically determined by use of x-rays of the patients spinal column or other osseous joint where malposition is present. From the results of such examination and measurement, the appropriate direction and amount of force to be applied, may be established by the practitioner.

This invention provides means for inputting the coordinates or the directions in which the complex energy force is to be applied as well as a display means which tells the practitioner when the instrument is properly aligned with the patient's vertebrae or other osseous joint. The instrument further provides means for setting the amplitude of the force to be applied, both linear and torque, and the direction of the torque component. The amount of force may be varied over a wide level and is applied with a unique complex waveform which may also be adjusted.

The force is not a single impact such as results from the release of a plunger held by a mechanical spring or electrical solenoid, but is rather a packet of waveforms of varying frequency and amplitude.

A microprocessor is utilized in the control means which allow adjustment of the sequence and variability of the waveform distribution within the complex energy wave, as well as the duration of its application. In this manner not only can the proper adjustment force be applied for the particular dislocation as revealed by the patient's x-rays, but the frequency and characteristics of the sequence of waveforms may be altered to produce the optimum adjustment for a particular patient's unique body characteristics.

The instrument may also be applied in orthopedic practice where osseous joint adjustment may be required.

BRIEF DESCRIPTION OF THE DRAWINGS

FIG. 2A shows the rear or top view of the hand held portion.

FIG. 3 shows the front or panel display view of the control portion of the spinal adjustment system.

FIG. 4 shows a detail of the stylus tip.

DETAILED DESCRIPTION OF THE PREFERRED EMBODIMENTS

Figure 1:
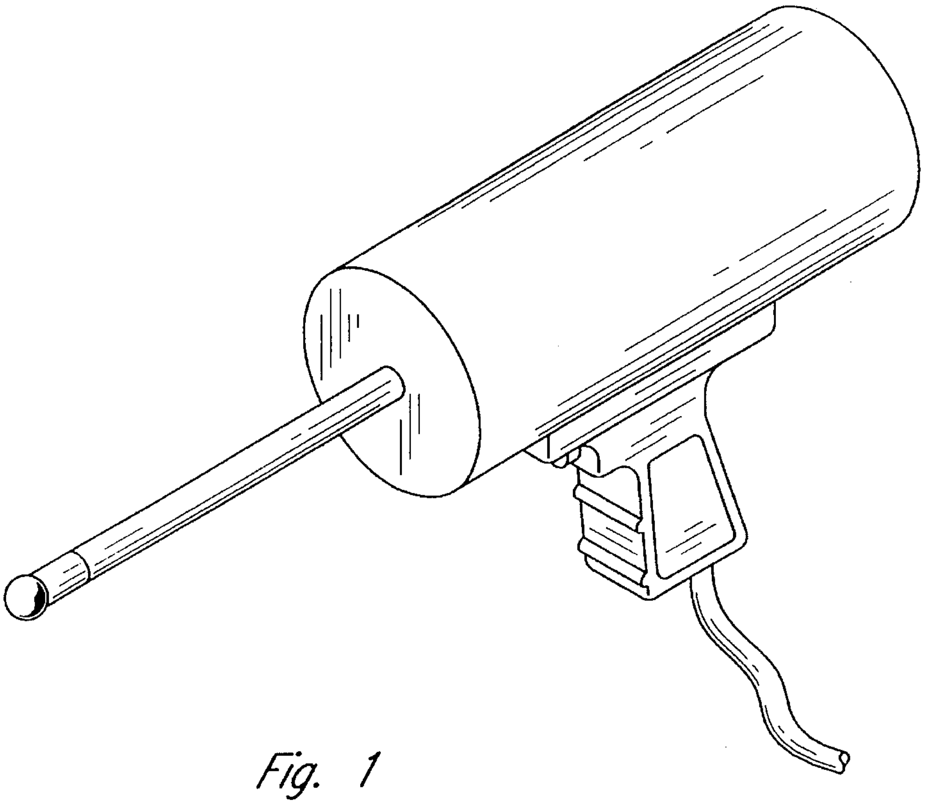
FIG. 1 shows a perspective view of the hand held portion of the spinal adjustment system.

The instrument described is embodied in two parts. One is a hand-held portion, FIG. 1, which includes the adjusting member, and the other is a controller and indicator which is in a separate housing, FIG. 3.

The adjusting portion is designed to be hand held but may also be mounted on a mounting means as necessary to reduce operator stress, if many patients are to be treated over an extended time period. In the preferred embodiment the adjusting portion consists of four parts, an elongated rod 10, with a stylus 11, at the end thereof which is placed in contact with the patient in the proximity of the vertebrae or other osseous joint to be adjusted; a central enclosed portion 12, which includes the voice coil mechanism and driving means to move the stylus assembly in the linear direction, two solenoids and their driving means to move the stylus assembly in the rotational direction; an indicating means 13, to show the alignment of the stylus with the axis as specified by the controller, FIG. 2A, and a pistol grip 14, with trigger means 15, for ease of handling the adjusting portion of the instrument.

The stylus in FIG. 4, is designed with a plurality of pins 16, for the purpose of transmitting torque forces, which may be in a clockwise or counterclockwise direction. The entire stylus assembly is attached to the voice coil and solenoid mechanisms within the body of the hand held portion.

The stylus assembly is designed to be as light as possible thus, in the preferred embodiment, carbon fiber is used. The tips are changeable to allow for a variety of shapes to impart the torque forces to the patient. In the preferred embodiment four one eighths inch diameter pins 16, rounded at the patient touching ends are utilized, the pins being spaced evenly about the center of the stylus end piece.

Figure 2:
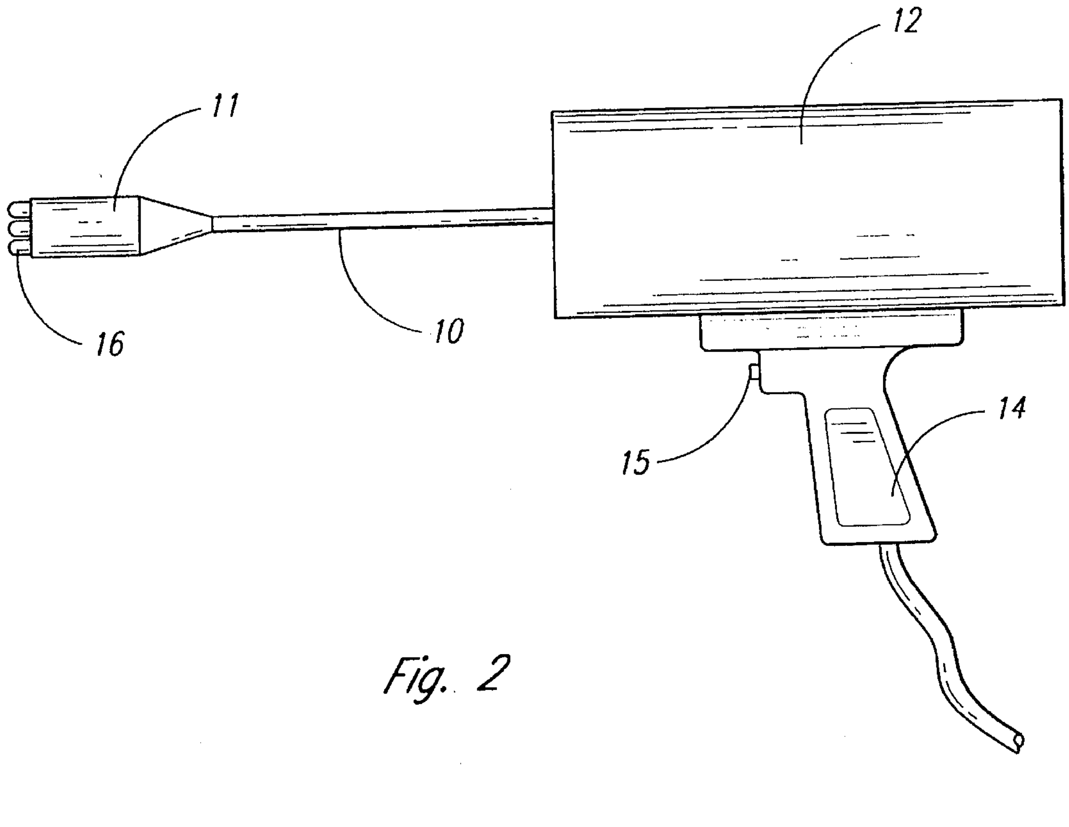
FIG. 2 shows a front side view of the hand held portion.

At the opposite end of the adjusting portion there are located a series of light emitting diodes (LED's) mounted in a cross configuration as shown in FIG. 2A. When the instrument is aligned in its longitudinal axis with the co-ordinates specified by the controller the center LED will be on. If the instrument deviates the other LED's will be lit to show the misalignment. Moving the instrument such that only the center LED is on, will indicate to the operator that the instrument is in proper alignment. The two axis sensor means which are commercially available are installed internally in the hand held portion of the instrument perpendicular to each other. A liquid crystal display means using a movable cursor could be implemented in lieu of the LED display.

Both the linear and rotational force applied to the patient by the stylus is such as to minimize discomfort to the patient, the procedure being non-invasive.

The design of the hand held portion is such as to minimize overall weight. Magnet means are required for operation of the voice coil driving means. The magnets used may be any of various commercially available magnets, with the highest flux density per unit weight preferred.

For ease of holding and aligning the hand held portion, a pistol grip 14, is attached to the device with a trigger means 15. The trigger allows for the activation of one sequence of impulses or packet or may be left on to provide multiple packets of the complex energy waveform.

The control and display means for the instrument are in a separate container which may be located on a stand in close proximity to the patient. FIG. 3 shows the front or display side of the control portion. The panel display contains two indicators 20, to show the vector components of both the linear and rotational forces to be applied, as well as two controls 21, with which the vector force components may be adjusted. The rotational force or torque may be applied in either a clockwise or a counter-clockwise direction and a switch 22, is located on the front panel of the control and display portion, to select the direction desired. In addition, the display includes a power on-off switch 23, and a cycle counter 24. The vector settings may be controlled or set within approximately ⅛" accuracy, and such settings will be shown on the display panel.

Internal to the control unit is a computer or microprocessor which transmits appropriate signals to orient the hand-held portion in the proper direction corresponding to the subluxation, as previously measured, of the patient.

The actual energy waveform is also controlled by the microprocessor and consists of a series of square waves of varying frequency and duration, to be transformed from electrical impulses generated in the control unit, to mechanical energy by the voice coil transducer in the hand held unit and transmitted to the patient via the stylus tip. Similarly the microprocessor generates the electrical waveforms to command the proper solenoid transducer to generate the torque component when required by the practitioner.

In the preferred embodiment one packet or series of impulses consist of a series of square waves varying in frequency from about 80 Hz down to 30 Hz followed by a sequence of 12 Hz square waves all within a time period of approximately 1 second.

What is claimed is:

1. An instrument for adjusting osseous joint subluxation comprising:

a portable portion, comprising a moveable stylus to be held adjacent to the patient in the proximity of the osseous joint to be adjusted, which stylus may move either laterally along the axis of the stylus or radially about the axis of the stylus, a central portion containing the driving means for imparting motion to the stylus, a means for holding said portable portion, and a display means to indicate when the said portable portion is properly aligned with the patient, said driving means comprising a means to actuate said moveable stylus in both linear and rotational direction, said stylus being activated by a series of specific square wave pulses, said pulse means generated in said driving means, and a fixed portion, comprising display and adjustment means, to set and display the lateral and radial components of the energy to be transmitted to the patient; the proper alignment of the portable portion of the instrument with the patient; generating means for said complex energy waveform to provide the desired signals to the stylus driving means and the power supply and switches to actuate and operate the instrument.

2. The method for adjusting osseous joint luxation and subluxation according to claim 1, wherein the means for generating said complex energy waveform is provided by the instrument according to claim 3 and said complex energy waveform comprises a series of specific square waves of varying frequency, the fundamental frequency of said square waves including the natural frequency of the structure in the proximity of the osseous joint being adjusted.

3. The instrument for adjusting osseous joint subluxation according to claim 1, wherein the stylus tip is equipped with a plurality of replaceable pins which transmit the radial component of the said complex energy waveform to the patient.

4. The instrument for adjusting osseous joint subluxation according to claim 1, wherein the stylus is made of carbon fiber.

5. The instrument for adjusting osseous joint subluxation according to claim 1 wherein the stylus linear force driving means is a voice coil.

6. The instrument for adjusting osseous joint subluxation according to claim 1, wherein the stylus rotational force driving means is accomplished by one or more solenoids.

7. The instrument for adjusting osseous joint subluxation according to claim 1, where the alignment of the instrument is displayed by a plurality of LEDs arranged in a cross hair arrangement and energized by sensor means internal to the portable portion of said instrument, such that alignment with the proper setting of the co-axial co-ordinate is indicated by the energizing of the central LED, and deviation from the proper setting by the energizing of the LEDs away from the center LED.

8. The instrument for adjusting osseous joint subluxation according to claim 1, wherein the characteristics of the complex energy waveform may be adjusted as to amplitude of each individual pulse waveform, pulse frequency, waveform shape, sate of change of frequency, repetition of waveforms, duration of individual pulses and duration of the waveform packet.

* * * * *

UNITED STATES PATENT AND TRADEMARK OFFICE

CERTIFICATE OF CORRECTION

PATENT NO. : 5,618,315

DATED : April 08, 1997

INVENTOR(S) : Thomas ELLIOTT

It is certified that error appears in the above-indentified patent and that said Letters Patent is hereby corrected as shown below:

Column 1, line 45, delete "fox" and substitute --for-- therefor;

Column 4, line 63, delete "sate" and substitute --rate-- therefor;

Cover Page, [56] References Cited U.S. PATENT DOCUMENTS, after

"4,841,955 6/1989 Evans et al. ."

insert the following two references:

| | | |
|---|---|---|
| --4,984,127 | 1/91 | Evans et al. |
| 5,159,922 | 11/92 | Mabuchi et al.-- |

Signed and Sealed this

Twenty-fourth Day of June, 1997

*Attest:*

BRUCE LEHMAN

*Attesting Officer* *Commissioner of Patents and Trademarks*